United States Patent
López-Cervantes et al.

(10) Patent No.: US 8,748,124 B2
(45) Date of Patent: Jun. 10, 2014

(54) BIODEGRADATION PROCESS AND COMPOSITION

(75) Inventors: Jamie López-Cervantes, Obregón (MX); Dalia Isabel Sánchez-Machado, Obregón (MX); Karl Reiner Fick Rochin, Los Naranjos (MX)

(73) Assignee: Agrinos AS, Lysaker (NO)

( * ) Notice: Subject to any disclaimer, the term of this patent is extended or adjusted under 35 U.S.C. 154(b) by 0 days.

(21) Appl. No.: 12/974,924

(22) Filed: Dec. 21, 2010

(65) Prior Publication Data

US 2011/0151508 A1 Jun. 23, 2011

Related U.S. Application Data

(60) Provisional application No. 61/289,706, filed on Dec. 23, 2009, provisional application No. 61/299,869, filed on Jan. 29, 2010, provisional application No. 61/355,365, filed on Jun. 16, 2010.

(51) Int. Cl.
  *C12P 39/00* (2006.01)
(52) U.S. Cl.
  USPC .......................................................... 435/42
(58) Field of Classification Search
  USPC .......................................................... 435/42
  See application file for complete search history.

(56) References Cited

U.S. PATENT DOCUMENTS

| | | |
|---|---|---|
| 4,195,175 A | 3/1980 | Peniston |
| 4,536,207 A | 8/1985 | McCandliss |
| 4,812,159 A | 3/1989 | Freepons |
| 4,915,944 A | 4/1990 | Chet et al. |
| 4,952,229 A | 8/1990 | Muir |
| 4,964,894 A | 10/1990 | Freepons |
| 4,970,150 A | 11/1990 | Yaku |
| 4,978,381 A | 12/1990 | Hadwiger |
| 5,208,159 A | 5/1993 | Toda |
| 5,266,096 A | 11/1993 | Slavensky |
| 5,288,488 A | 2/1994 | Backman |
| 5,374,627 A | 12/1994 | Ito et al. |
| 5,567,325 A | 10/1996 | Townsley |
| 5,733,851 A | 3/1998 | Villanueva |
| 5,776,448 A | 7/1998 | Suslow |
| 5,965,545 A | 10/1999 | Ben-Shalom |
| 5,998,173 A | 12/1999 | Haynes et al. |
| 6,060,429 A | 5/2000 | Ben-Shalom |
| 6,167,652 B1 | 1/2001 | Heinsohn |
| 6,232,270 B1 | 5/2001 | Branly |
| 6,255,085 B1 | 7/2001 | Chen |
| 6,407,040 B1 | 6/2002 | Nichols |
| 6,524,998 B1 | 2/2003 | Kloepper |
| 6,589,942 B1 | 7/2003 | Ben-Shalom |
| 6,649,566 B2 | 11/2003 | Doostdar |
| 6,896,809 B2 | 5/2005 | Qian |
| 6,972,284 B2 | 12/2005 | Fan |
| 7,241,463 B2 | 7/2007 | Nielsen |
| 7,811,353 B2 | 10/2010 | Blais |
| 2002/0000540 A1 | 1/2002 | Smither-Kopperl |
| 2003/0185939 A1* | 10/2003 | Nielsen ........................... 426/61 |
| 2004/0228844 A1 | 11/2004 | Isayama |
| 2007/0122869 A1* | 5/2007 | Hasegawa et al. .............. 435/34 |
| 2008/0318777 A1 | 12/2008 | Lin et al. |
| 2010/0267999 A1 | 10/2010 | Lau et al. |
| 2012/0084886 A1 | 4/2012 | Lopez-Cervantes et al. |

FOREIGN PATENT DOCUMENTS

| | | |
|---|---|---|
| CN | 101139223 A | 3/2008 |
| CN | 101422210 A | 5/2009 |
| CN | 101564081 A | 10/2009 |
| EP | 0328383 A1 | 8/1989 |
| EP | 1142988 A1 | 10/2001 |
| JP | 8 157310 | 6/1996 |
| JP | 9 143013 | 6/1997 |
| JP | 2003160420 A | 6/2003 |
| KR | 20050117990 A | 12/2005 |
| KR | 20090085754 A | 8/2009 |
| WO | WO 8907395 A1 | 8/1989 |
| WO | WO 9709879 A1 | 3/1997 |
| WO | WO 2009031874 A1 | 3/2009 |
| WO | WO 2011076759 A1 | 6/2011 |
| WO | WO 20111157747 | 12/2011 |
| WO | WO 2012/175739 | 12/2012 |

OTHER PUBLICATIONS

Bhaskar et al. Shrimp biowaste fermentation with *Pediococcus acidolactici*CFR2182: Optimization of fermentation conditions by response surface methodology and effect of optimized conditions on deproteination/demineralization and carotenoid recovery. Enzyme and Microbial Technology. 2007;40:1427-1434.*

Rojas-Avelizapa et al. Selection and characterization of a proteo-chitinolytic strain of *Bacillus thuringiensis*, able to grow in shrimp waste media. World Journal of Microbiology & Biotechnology. 1999;15:299-308.*

Rao et al. Chitin production by Lactobacillus fermentation of shrimp biowaste in a drum reactor and its chemical conversion to chitosan. J Chem Technol Biotechnol. 2005;80:1080-1087.*

Faid et al. Biotransformation of fish waste into a stable feed ingredient. Food Chemistry. 1997;60(1):13-18.*

Rossland et al. Influence of controlled lactic fermentation on growth and sporulation of *Bacillus cereus*in milk. International Journal of Food Microbiology. 2005;103:69-77.*

Microtack. Aquaculture nitrifiers. Microtack Organic Aquaculture & Wastewater Treatment Supplies. 2002;1.*

Hoster et al. Enrichment of chitinolytic microorganisms: isolation and characterization of a chitinase exhibiting antifungal activity against phytopathogenic fungi from a novel Streptomyces strain. Appl Microbiol Biotechnol. 2005;66:434-442.*

(Continued)

*Primary Examiner* — Ruth Davis
*Assistant Examiner* — Lynn Y Fan
(74) *Attorney, Agent, or Firm* — Morgan, Lewis & Bockius LLP

(57) ABSTRACT

Disclosed are novel microbial compositions and biodegradation processes to treat marine animal or marine animal by-products to produce solid, liquid and lipid fractions that contain useful compounds.

14 Claims, 2 Drawing Sheets

(56) References Cited

OTHER PUBLICATIONS

Jurgensen et al. Nonsymbiotic nitrogen-fixing micro-organisms in forest and tundra soils. Plant and Soil. 1971;34:341-356.*
Bhaskar, N. et al., "Shrimp biowaste fermentation with *Pediococcus acidolactici*CFR2182: Optimization of fermentation conditions by response surface methodology and effect of optimized conditions on deproteination/demineralization and carotenoid recovery", *Enzyme and Microbial Techn.*40, 1427-1434 (2007).
Choorit, Wanna et al. "Use of response surface method for the determination of demineralization efficiency in fermented shrimp shells" *Bioresource Techn.*99, pp. 6168-6173 (2008).
Cira, Luis et al., "Pilot scale lactic acid fermentation of shrimp wastes for chitin recovery" *Process Biochemistry*37, 1359-1366, (2002).
Healy, M. et al., "Environmental monitoring and biodiagnostics of hazardous contanimants" 27-40.
Jung, W.J. et al., "Demineralization of red crab shell waste by lactic acid fermentation" *Appl. Microbiol. Biotechnol.*67: 851-854 (2005).
Jung, W.J. et al., "Extraction of chitin from red crab shell waste by cofermentation with *Lactobacillus paracasei subsp. tolerans*KCTC-3074 and *Serratia marcescens*FS-3", *Appl. Microbiol Biotechnol*71: 234-237 (2006).
Jung, W.J. et al., "Production of chitin from red crap shell waste by successive fermentation with *Lactobacillus paracasei*KCTC-3074 and *Serratia marcescens*FS-3", *Carbohydrate Polymers*68, 746-750 (2007).
Khanafari, A. et al. "Extraction of Astaxanthin Esters From Shrimp Waste by Chemical and Microbial Methods" *Iran J. Environ. Health Sci. Eng.*vol. 2, No. 2, pp. 93-98 (2007).
Lopez-Cervantes, J. et al., "Analysis of free amino acids in fermented shrimp waste by high-performance liquid chromatography" *J. Of Chromatography A*, 1105, 106-110 (2006).
Lopez-Cervantes, J. et al., "High-performance liquid chromatography method for the simultaneous quantification of retinol, alpha-tocopherol, and cholesterol in shrimp waste hydrolysate" *J. Of Chromatography*A, 1105, 135-139 (2006).
Lopez-Cervantes, J. et al., "Quantification of astaxanthin in shrimp waste hydrolysate by HPLC" *Biomedical Chromatagraphy*, 20: 981-984 (2006).
Lopez-Cervantes, J. et al., "Quantification of glucosamine from shrimp waste using HPLC" *J. of Chromatagraphic Sci.*, 45, 195-199 (2007).
Pacheco, Neith et al. "Effect of temperature on chitin and astaxanthin recoveries from shrimp waste using lactic acid bacteria",*Bioresource Techn.*100, pp. 2849-2854 (2009).
Rao, M.S. et al., "Critical factors in chitin production by fermentation of shrimp biowaste" *Appl. Microbiol. Biotechnol.*54: 808-813 (2000).
Rao, M.S. et al., "Fermentation of shrimp biowaste under different salt concentrations with amylolytic and non-amylolytic *Lactobacillus*strains for chitin production" *Food Technol. Biotechnol.*44(1) 83-87 (2006).
Rojas-Avelizapa et al., "Selection and chracterization of a proteo-chitinolytic strain of *Bacillus thuringensis*, able to grow in shrimp waste media" *World J. Of Microbiol. & Biotechnol.*15: 299-308 (1999).
Sachindra, N.M. et al., "Recovery of carotenoids from ensilaged shrimp waste", *Bioresource Techn.*98, pp. 1642-1646 (2007).
Sanchez-Machado, Dalia Isabel et al., "High-performance liquid chromatography with fluourescence detection for quantification of tryptophan and tyrosine in a shrimp waste protein concentrate" *J. Chromatography B*, 863, 88-93 (2008).
Sanchez-Machado, Dalia Isabel et al., "Quantification of organic acids in fermented shrimp waste by HPLC" *Food Technol. Biotechnol.*, 46, (4) 456-460 (2008).
Shirai, Keiko et al. "Effect of initial glucose concentration and inoculation level of lactic acid bacteria in shrimp waste insilation" *Enzyme and Microbial Techn.*28, 446-452 (2001).
Sini, et al., "Study on the production of chitin and chitosan from shrimp shell by using *Bacillus subtilis*fermentation" *Carbohydrate Research*342, pp. 2423-2429 (2007).
Sorokulova, I. et al. "Effficient decomposition of shrimp shell waste using *Bacillus cereus*and *Exiguobacterium acetylicum*" *J. Ind. Microbiol. Biotechnol.*36: 1123-1126 (2009).
Waldeck, J. et al. "Isolation and molecular characterization of chitinase-deficient *Bacillus licheniformis*strains capable of deproteinization of shrimp shell waste to obtain highly viscous chitin" *Applied and Environ. Microbiol.*, vol. 72, No. 12, pp. 7879-7885 (2006).
Bueno-Solano, et al, "Chemical and biological characteristics of protein hydrolysates from fermented shrimp by-products", 2009, Food Chemistry, vol. 112, No. 3, pp. 671-675.
Boyer, Joseph "Aerobic and Anaerobic Degradation and Minderalization of $^{14}$C-Chitin by Water col. And Sediment Inocula of the York River Esturary, Virginia" (1994) *Applied and Environ. Microbio.*vol. 60, No. 1, pp. 174-179.
Xu, Y. et al. "Chitin purification from shrimp wastes by microbial deproteination and decalcification" (2008) *Appl. Microbiol. Biotechnol.*vol. 79:687-697.
Amar, Beatrice "Fermentation of Prawn Shell Waste and Application of its Product as Dietary Ingredient for the Indian White Prawn *Penaeus Indicus*(H. Milne Edwards)" Thesis submitted to Cochin University of Science and Technology (2001) with Synopsis.
Aye and Stevens "Technical Note: Improved chitin production by pretreatment of shrimp shell", *Journal of Chemical Tech and Biotech*(2004) vol. 79: 421-425.
Bhattacharya, et al. "Bacterial Chinases: Properties and Potential" (*Critical Reviews in Biotechnology*, (2007) vol. 27:21-28.
Boyer, Joseph "Aerobic and Anaerobic Degradation and Minderalization of $^{14}$C-Chitin by Water Column and Sediment Inocula of the York River Esturary, Virginia" *Applied and Environ. Microbio.*(1994) vol. 60, No. 1, pp. 174-179.
Campbell et al. "A study of Chitin-decomposing Micro-organisms of Marine Origin" *Journal of General Microbiology*, (1951) vol. 5:894-905.
Cody et al. "Distribution of Chitinase and Chitobiase in Bacillus", *Current Microbiology*(1989) vol. 19:201-205.
Nandakumar, et al. "Chitinolytic Activity of Native Pseudomonas fluorescens Srains"*Journal of Agriculture Science Technology*vol. 9:61-68.
Xu, Y. et al. "Chitin purification from shrimp wastes by microbial deproteination and decalcification" *Appl. Microbiol. Biotechnol.* (2008) vol. 79:687-697.
Binod, Parameswaran et al., "Fungal Biosynthesis of Endochitinase and Chitobiase in Solid state Fermentation and their Application for the Production of N-Acetyl-d-Glucosamine from Colloidal Chitin," Bioresource Technology, 98 (2007) 2742-2748.
Kandra, Prameela et al., "Efficent Use of Shrimp Waste: Present and Future Trends," Appl Microbiol Biotechnol (2012) 93:17-29.

* cited by examiner

BIODEGRADATION PROCESS AND COMPOSITION

This application claims the benefit of U.S. Provisional Application Ser. Nos. 61/289,706, filed Dec. 23, 2009, 61/299,869, filed Jan. 29, 2010, and 61/355,365, filed Jun. 16, 2010 under 35 U.S.C. §119(e) and are expressly incorporated herein by reference.

TECHNICAL FIELD

Disclosed are novel microbial compositions and microbial processes to treat marine animal by-products and in some cases the entire marine animal to produce solid, liquid and lipid fractions that contain useful compounds.

BACKGROUND OF THE INVENTION

The processing of fish and marine arthropods, such as shrimp, crab and crayfish, produces large quantities of marine by-products. Most are used in low end products such as fertilizers, fish silage or pet food but the unused by-products pose an economic burden for the marine product processing industries because of the need to dispose of such residues in an environmentally sound way. By some estimates such by-products represent 25% of the total production captured by fisheries.

For example, during the processing of shrimp for its subsequent freezing and marketing, a large amount of remains are generated since 35% of the animal is inedible and must be discarded. These remnants or by-products are composed of the shrimp's cephalothorax and exoskeleton. However, these shrimp by-products are rich in high-value substances, such as chitin, protein, lipids, carotenoid pigments (astaxanthine) and minerals. The majority of the inedible by-products are disposed at landfills or dumped back into the ocean, thus causing serious environmental problems and considerable losses to the shrimp processing industry. At present, only a small amount of these by-products are used as a supplement for animal feed.

The most common technique for shrimp by-product utilization is sun drying. This technique has low hygienic control and the products are used primarily for animal consumption. Other methods employ chemical acids and alkalis at different concentrations, temperatures and times for the extraction of chitin and recovery of protein hydrolysates. However, these methods cause a depolymerization and partial deacetylation of the chitin. Moreover, these methods complicate the recovery of other products, such as protein and pigment.

Enzymatic methods have been developed for the extraction of chitin, liquid hydrolysates and pigments. Such methods use enzymatic extracts or enzyme isolates. Other studies have reported the use of microbial enzymes, such as commercial alcalase, for the extraction of proteins from shrimp and marine animal by-products. The combination of alcalase and pancreatin has been reported for the extraction of chitin, hydrolyzed protein and pigmented lipids.

Lactic fermentation processes have been used as a substitute for the above chemical and enzymatic processes. Fermentation represents a cost effective technique which stabilizes and retains the nutritional quality of the by-products. The optimal conditions for fermentation depend on several factors including the choice and concentration of carbohydrates, pH, temperature, time, and the choice of aerobic or anaerobic conditions. Another important factor is the choice of microorganism and initial inoculum concentration. To facilitate the fermentation process of shrimp by-products pure cultures of lactic acid bacteria (LAB) have been used. Such LAB include *Lactobacillus plantarum* (Rao, M. S., Stevens, W. F., 2006, "Fermentation of shrimp biowaste under different salt concentrations with amylolytic and non-amylolitic *Lactobacillus* strains for chitin production," *Food Technology and Biotechnology* 44, 83-87; Rao, M. S., Muñoz, J., Stevens, W. F., 2000, "Critical factors in chitin production by fermentation of shrimp biowaste," *Applied Microbiology and Biotechnology* 54, 808-813; Bhaskar, N., Suresh, P. V., Sakhare, P. Z., Sachindra, N. M., 2007, "Shrimp biowaste fermentation with *Pediococcus acidolactici* CFR2182: optimization of fermentation conditions by response surface methodology and effect of optimized conditions on deproteination/demineralization and carotenoid recovery," *Enzyme and Microbial Technology* 40, 1427-1434), *Lactobacillus* sp. B2 (Circ, L. A., Huerta, S., Hal, G. M., Shirai, K., 2002, "Pilot scale lactic acid fermentation of shrimp waste for chitin recovery," *Process Biochemistry* 37, 1359-1366; Shirai, K., Guerrero, I., Huerta, S., Saucedo, G., Castillo, A., Gonzalez, R. O., Hall, G. M., 2001, "Effect of initial glucose concentration and inoculation level of lactic acid bacteria in shrimp waste ensilation," *Enzyme and Microbial Technology* 28, 446-452), *Lactobacillus casei* (Shirai 2001), *Lactobacillus paracasei* (Jung, W. J., Jo, G. H., Kuk, J. H., Kim, Y. J., Oh, K. T., Park, R. D., 2007, "Production of chitin from red crab shell waste by successive fermentation with *Lactobacillus paracasei* KCTC-3074 and *Serratia marcescens* FS-3," *Carbohydrate Polymers* 68, 746-750), *Lactobacillus pentosus* (Bautista, J., Jover, M., Gutierrez, J. F., Corpas, R., Cremades, O., Fontiveros, E., Iglesias, F., Vega, J., 2001, "Preparation of crayfish chitin by in situ lactic acid production," *Process Biochemistry* 37, 229-234; Shirai 2001), *Lactobacillus acidophilus* B4495 and *Lactobacillus lactis* (Bhaskar 2007), *Lactobacillus salvarus* (Beaney 2005), *Enteroccus facium* (Beaney 2005), *Pedioccoccus acidilactici* (Bhaskar 2007) and *Pedioccoccus* sp. L1/2 (Choorit, W., Patthanamanee, W., Manurakchinakorn, S., 2008, "Use of response surface method for the determination of demineralization efficiency in fermented shrimp shells," *Biores. Technol.* 99, 6168-6173). In addition, a mixture of four LAB has been used (Bhaskar 2007) and there are reports using *Lactobacillus* in combination with *Serratia marcescens* FS-3 (Jung 2007) or *Staphylococcus carnosus* (Shirai 2001). However, the industrialization of such fermentation processes has not been successful due the poor performance of commercial inoculants.

Lactic fermentation of shrimp by-products produces protein hydrolysates, chitin, minerals, and lipids. Chitin and its deacetylated derivatives have many applications in agriculture, biomedicine, food and the paper industry, while liquid hydrolysate is an excellent source of essential amino acids that can be used for human or animal consumption. The lipidic paste contains sterols, vitamin A and E, and carotenoid pigments such as astaxanthin which can be used in feed for salmonoids or as a natural coloring in the food industry.

Chitin is a natural polysaccharide found particularly in the exoskeleton of crustaceans, the cuticles of insects, and the cell walls of fungi. Because chitin is one of the most abundant biopolymers, much interest has been paid to its biomedical, biotechnological and industrial applications. Chitosans are poly-($\beta$-1-4)-N-acetyl-D-glucosamine compounds produced by the deacetylation of chitin ($\beta$-1-4)-N-acetyl-D-glucosamine. Glucosamine is an amino monosaccharide obtained by de-polymerization of chitosan. It participates in the constitution of glycosaminoglycans, a major class of extracellular complex polysaccharides. Glucosamine sulphate, glucosamine hydrochloride and N-acetyl-glucosamine are commonly used alone or as part of a mixture.

Generally, the liquid hydrolysate has a high content of essential amino acids, indicating a high nutritional value that justifies its use as a supplement for animal and aquaculture nutrition or as a nitrogen source in growth media for microorganisms. Additionally, these hydrolysates are a source of free amino acids and can be used for nutrition in plants as a biostimulant.

Astaxanthine (3,3'-dihydroxy-β,β-carotene-4,4'-dione), a ketocarotenoid oxidized from β-carotene, naturally occurs in a wide variety of marine and aquatic organisms. Due to its attractive pink color, its biological functions as a vitamin A precursor, and antioxidative activity, astaxanthine can be used as a colorant in food and in medicine. In the structure of astaxanthine, two identical asymmetric carbon atoms at C3 and C3' are found. However trans-asthaxanthine is the quantitatively most prevalent carotenoid in crustacean species.

References disclosing these and other products from lactic fermentation include: Sanchez-Machado et al. "Quantification of organic acids in fermented shrimp waste by HPLC" *Food Technology and Biotechnology*, volume 46, 456 (2008); Sanchez-Machado et al. "High-performance liquid chromatography with fluorescence detection for quantitation of tryptophan and tyrosine in a shrimp waste protein concentrate", *Journal of Chromatography B*, volume 863, 88 (2008); Lopez-Cervantes et al., "Quantitation of glucosamine from shrimp waste using HPLC" *Journal of Chromatographic Science*, volume 45, 1 (2007); Lopez-Cervantes et al., "Quantification of astaxanthin in shrimp waste hydrolysate by HPLC" *Biomedical Chromatography*, volume 20, 981 (2006); Lopez-Cervantes et al., "High-performance liquid chromatography method for the simultaneous quantification of retinol, alpha-tocopherol, and cholesterol in shrimp waste hydrolysate" *Journal of Chromatography A*, volume 1105, 1-2 (2006); Lopez-Cervantes et al., "Analysis of free amino acids in fermented shrimp waste by high-performance liquid chromatography", *Journal of Chromatography A*, volume 1105, 1 (2006).

SUMMARY OF THE INVENTION

Disclosed are microbial compositions and biodegradation processes.

One microbial composition comprises (a) one or more lactic acid bacteria (LAB) and (b) one or more or two or more microorganisms selected from the group of genera consisting of *Bacillus*, *Azotobacter*, *Trichoderma*, *Rhizobium*, *Clostridium*, *Pseudomonas*, *Streptomyces*, *Micrococcus*, *Nitrobacter* and *Proteus*. In preferred embodiments at least one of the *Bacillus*, *Azotobacter*, *Trichoderma*, *Rhizobium*, *Clostridium*, *Pseudomonas*, *Streptomyces*, *Micrococcus*, *Nitrobacter* and *Proteus* is a chitinolytic strain that produces a chitinase (e.g. endochitinase and/or exochitinase). In some microbial compositions the LAB is selected from the genera consisting of *Lactobacillus*, *Pediococcus*, *Lactococcus*, and *Streptococcus*. When the LAB is *Lactobacillus*, it is preferred that the LAB is *Lactobacillus acidophilus* and/or *Lactobacillus casei*, more preferably *Lactobacillus acidophilus* (Bioderpac, 2008) and *Lactobacillus casei* (Bioderpac, 2008).

The *Bacillus* in this composition is preferably selected from the group consisting of *Bacillus subtilis*, *Bacillus cereus*, *Bacillus megaterium*, *Bacillus licheniformis* and *Bacillus thuringiensis*, more preferably *Bacillus subtilis* (SILoSil® BS), *Bacillus cereus* (Bioderpac, 2008), *Bacillus licheniformis*(Bioderpac, 2008) and *Bacillus thuringiensis* strains HD-1 and HD-73 (SILoSil®BT).

The *Azotobacter* in this composition is preferably *Azotobacter vinelandii*, more preferably *Azotobacter vinelandii* (Bioderpac, 2008).

The *Trichoderma* in this composotion is preferably *Trichoderma harzianum*, more preferably *Trichoderma harzianum* (TRICHOSIL)

The *Rhizobium* in this composition is preferably *Rhizobium japonicum*, more preferably *Rhizobium japonicum* (Bioderpac, 2008).

The *Clostridium* in this composition is preferably *Clostridium pasteurianu*, more preferably *Clostridium pasteurianu* (Bioderpac, 2008).

The *Pseudomonas* in this composition is preferably *Pseudomonas fluorescens*, more preferably *Pseudomonas fluorescens* (Bioderpac, 2008).

Another microbial composition comprises one or more or two or more microorganisms selected from the group consisting of *Bacillus subtilis* ((SILoSil®BS), *Bacillus cereus* (Bioderpac, 2008), *Bacillus megaterium* (Bioderpac, 2008), *Azotobacter vinelandii* (Bioderpac, 2008), *Lactobacillus acidophilus* (Bioderpac, 2008), *Lactobacillus casei* (Bioderpac, 2008), *Trichoderma harzianum* (TRICHOSIL), *Rhizobium japonicum* (Bioderpac, 2008), *Clostridium pasteurianum* (Bioderpac, 2008), *Bacillus licheniformis* (Bioderpac, 2008), *Pseudomonas fluorescens* (Bioderpac, 2008), *Bacillus thuringiensis* strains HD-1 and HD-73 (SILoSil® BT), *Streptomyces* (Bioderpac, 2008), *Micrococcus* (Bioderpac, 2008), *Nitrobacter* (Bioderpac, 2008) and *Proteus* (Bioderpac, 2008).

Another embodiment of a microbial composition of comprises *Lactobacillus acidophilus* (Bioderpac, 2008) and/or *Lactobacillus casei* (Bioderpac, 2008).

A particularly preferred microbial composition comprises *Bacillus subtilis* (SILoSil® BS), *Bacillus cereus* (Bioderpac, 2008), *Bacillus megaterium* (Bioderpac, 2008), *Azotobacter vinelandii* (Bioderpac, 2008), *Lactobacillus acidophilus* (Bioderpac, 2008), *Lactobacillus casei* (Bioderpac, 2008), *Trichoderma harzianum* (TRICHOSIL), *Rhizobium japonicum* (Bioderpac, 2008), *Clostridium pasteurianum* (Bioderpac, 2008), *Bacillus licheniformis* (Bioderpac, 2008), *Pseudomonas fluorescens* (Bioderpac, 2008), *Bacillus thuringiensis* strains HD-1 and HD-73, *Streptomyces* (Bioderpac, 2008), *Micrococcus* (Bioderpac, 2008), *Nitrobacter* (Bioderpac, 2008) and *Proteus* (Bioderpac, 2008).

A preferred microbial composition is HQE. HQE was deposited with the American Type Culture Collection (ATCC) Manassas, Va., USA on Apr. 27, 2010 and given Patent Deposit Designation PTA-10861.

Also disclosed are isolated microorganisms selected from the group consisting of *Bacillus subtilis* (SILoSil® BS), *Bacillus cereus* (Bioderpac, 2008), *Bacillus megaterium* (Bioderpac, 2008), *Azotobacter vinelandii* (Bioderpac, 2008), *Lactobacillus acidophilus* (Bioderpac, 2008), *Lactobacillus casei* (Bioderpac, 2008), *Trichoderma harzianum* (TRICHOSIL), *Rhizobium japonicum* (Bioderpac, 2008), *Clostridium pasteurianum* (Bioderpac, 2008), *Bacillus licheniformis* (Bioderpac, 2008), *Pseudomonas fluorescens* (Bioderpac, 2008), *Bacillus thuringiensis* strains HD-1 and HD-73 (SILoSil® BT), *Streptomyces* (Bioderpac, 2008), *Micrococcus* (Bioderpac, 2008), *Nitrobacter* (Bioderpac, 2008) and *Proteus* (Bioderpac, 2008).

The biodegradation process comprises mixing a marine animal or marine animal by-product with any of the aforementioned microbial compositions to form a mixture; fermenting the mixture; and separating the mixture into solid, aqueous and lipid fractions. Unlike prior art biodegradation processes, the disclosed biodegradation process produces chitosan and glucosamine which can be found in the aqueous fraction. The marine animal is preferably a marine arthropod, such as shrimp, crayfish, crab or krill. In some embodiments the marine animal is fish or a fish by product such as fish skin, muscle or organ.

DETAILED DESCRIPTION OF THE INVENTION

Figure 1:
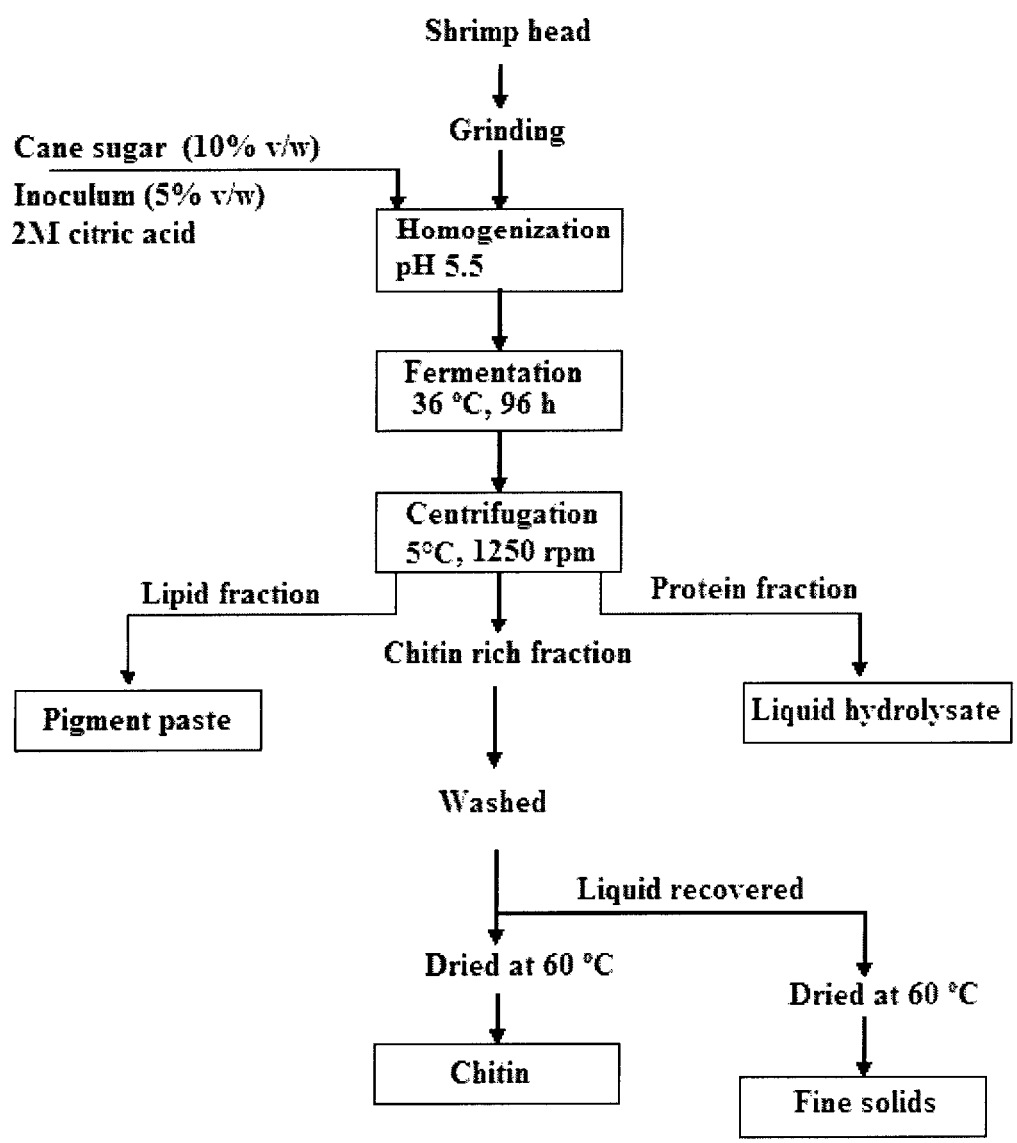
FIG. 1 schematically shows a preferred degradation process for shrimp by-products.

As used herein, the term "marine animal" refers to any animal that lives in oceans, seas or fresh water. Marine animals include fish and marine arthropods.

As used herein the term "marine arthropod" refers to an invertebrate marine animal having an exoskeleton that lives in oceans, seas or fresh water. Generally marine arthropods have a segmented body, and jointed appendages. Marine arthropods are members of the subphylum Crustacea. Preferred classes of Crustacea include Branchiopoda (e.g. brine shrimp, Cladocera and Triops), Cephalocardia (e.g. horseshoe shrimp), Maxillopoda (e.g. barnacles and copepods (zooplankton)), Ostracoda (e.g. ostracods) and Malacostraca (e.g. crab, lobsters, shrimp, krill etc.).

As used herein, the term "by-product" refers to any part of a marine animal. In some embodiments, the by-product is produced by the commercial processing of the marine animal. For example, in the shrimp industry, the cephalothorax and exoskeleton are shrimp by-products. In the crab and lobster processing industry the exoskeleton (shell) is a by-product.

In some embodiments, the entire arthropod can be used in the biodegradation process. For example, many krill are about 1-2 centimeters (0.4-0.8 in) long as adults but a few species grow to sizes on the order of 6-15 centimeters (2.4-5.9 in). Krill oil contains at least three components: (1) omega-3 fatty acids similar to those in fish oil, (2) omega-3 fatty acids conjugated to phospholipids and (3) the antioxidant astaxanthin. In addition, the exoskeleton contains fluoride. Accordingly, these components can be separated in the biodegradation process with the oil components being isolated in the lipid fraction and the fluoride in the liquid fraction.

As used herein the term "microbial composition" refers to a liquid, solid or gelatinous medium containing or physically supporting one or more microorganisms, preferably two or more. Microbial compositions include, but are not limited to, fermentation broths containing one or more microorganism(s) and inoculums which are generally used to start a fermentation broth and which contain a higher concentration of the microorganisms than which are present in the fermentation broth. Microbial compositions containing species/strains are sometimes referred to as "Bioderpac microbial compositions" which refers to a composition containing one or more of the microorganisms or a combination of one or more microorganisms with other microorganisms.

As used herein the term "isolated microorganism" refers to a liquid, solid or gelatinous medium containing or physically supporting one microorganism.

The disclosed microbial compositions or isolated microorganisms can be combined with other microorganisms to form a new microbial composition which can be used for processes other than those specifically disclosed herein. The selection of disclosed microorganism(s) will depend on its biological properties (e.g. production of protein or carbohydrate or chitin degrading enzymes), the other microorganisms selected and the process in which the combination is to be used. The selection of such components and processes will be apparent to the skilled artisan following the disclosure herein.

One microbial composition comprises (a) one or more lactic acid bacteria (LAB) and (b) one or more or two or more microorganisms selected from the group of genera consisting of *Bacillus, Azotobacter, Trichoderma, Rhizobium, Clostridium, Pseudomonas, Streptomyces, Micrococcus, Nitrobacter* and *Proteus*. In preferred embodiments at least one or more, two or more or three or more of the *Bacillus, Azotobacter, Trichoderma, Rhizobium, Clostridium, Pseudomonas, Streptomyces, Micrococcus, Nitrobacter* and *Proteus* is a chitinolytic strain that produces a chitinase (e.g. endochitinase and/or exochitinase). In some microbial compositions the LAB is selected from the genera consisting of *Lactobacillus, Pediococcus, Lactococcus,* and *Streptococcus*. When the LAB is *Lactobacillus,* it is preferred that the LAB is *Lactobacillus acidophilus* and/or *Lactobacillus casei,* more preferably *Lactobacillus acidophilus* (Bioderpac, 2008) and *Lactobacillus casei* (Bioderpac, 2008).

The *Bacillus* in this composition is preferably selected from the group consisting of *Bacillus subtilis, Bacillus cereus, Bacillus megaterium, Bacillus licheniformis* and *Bacillus thuringiensis*, more preferably *Bacillus subtilis* (SI-LoSil® BS), *Bacillus cereus* (Bioderpac, 2008), *Bacillus licheniformis* (Bioderpac, 2008) and *Bacillus thuringiensis* strains HD-1 and HD-73 (SILoSil® BT).

The *Azotobacter* in this composition is preferably *Azotobacter vinelandii,* more preferably *Azotobacter vinelandii* (Bioderpac, 2008).

The *Trichoderma* in this composotion is preferably *Trichoderma harzianum,* more preferably *Trichoderma harzianum* (TRICHOSIL).

The *Rhizobium* in this composition is preferably *Rhizobium japonicum,* more preferably *Rhizobium japonicum* (Bioderpac, 2008).

The *Clostridium* in this composition is preferably *Clostridium pasteurianu,* more preferably *Clostridium pasteurianu* (Bioderpac, 2008).

The *Pseudomonas* in this composition is preferably *Pseudomonas fluorescens,* more preferably *Pseudomonas fluorescens* (Bioderpac, 2008).

Another microbial composition comprises one or more or two or more microorganisms selected from the group consisting of *Bacillus subtilis* ((SILoSil® BS), *Bacillus cereus* (Bioderpac, 2008), *Bacillus megaterium* (Bioderpac, 2008), *Azotobacter vinelandii* (Bioderpac, 2008), *Lactobacillus acidophilus* (Bioderpac, 2008), *Lactobacillus casei* (Bioderpac, 2008), *Trichoderma harzianum* (TRICHOSIL), *Rhizobium japonicum* (Bioderpac, 2008), *Clostridium pasteurianum* (Bioderpac, 2008), *Bacillus licheniformis* (Bioderpac, 2008), *Pseudomonas fluorescens* (Bioderpac, 2008), *Bacillus thuringiensis* strains HD-1 and HD-73 (SILoSil® BT), *Streptomyces* (Bioderpac, 2008), *Micrococcus* (Bioderpac, 2008), *Nitrobacter* (Bioderpac, 2008) and *Proteus* (Bioderpac, 2008).

Another embodiment of a microbial composition of comprises *Lactobacillus acidophilus* (Bioderpac, 2008) and/or *Lactobacillus casei* (Bioderpac, 2008).

A particularly preferred microbial composition comprises *Bacillus subtilis* ((SILoSil® BS), *Bacillus cereus* (Bioderpac, 2008), *Bacillus megaterium* (Bioderpac, 2008), *Azotobacter vinelandii* (Bioderpac, 2008), *Lactobacillus acidophilus* (Bioderpac, 2008), *Lactobacillus casei* (Bioderpac, 2008), *Trichoderma harzianum* (TRICHOSIL), *Rhizobium japonicum* (Bioderpac, 2008), *Clostridium pasteurianum* (Bioderpac, 2008), *Bacillus licheniformis* (Bioderpac, 2008), *Pseudomonas fluorescens* (Bioderpac, 2008), *Bacillus thuringiensis* strains HD-1 and HD-73 (SILoSil® BT), *Streptomyces* (Bioderpac, 2008), *Micrococcus* (Bioderpac, 2008), *Nitrobacter* (Bioderpac, 2008) and *Proteus* (Bioderpac, 2008).

The preferred microbial composition for use in the biodegradation process is HQE. HQE was deposited with the American Type Culture Collection (ATCC) Manassas, Va., USA on Apr. 27, 2010 and given Patent Deposit Designation PTA-10861. HQE is a microbial consortium made up of microorganisms derived from fertile soils and microorganisms from commercial sources. The microorganisms form commercial sources include *Bacillus subtilis* (SILoSil® BS), *Bacillus thuringiensis* strains ND-1 and HD-73 (SILoSil® BT) and *Trichoderma harzianum* each obtained from Biotecnologia Agroindustrial S.A. DE C.V., Morelia, Michoacan, Mexico Microorganisms designated "Bioderpac 2008" by strain or species and strain can be derived from HQE. However, subsets of the microorganisms in HQE can also be used. The *Bacillus subtilis* (SILoSil® BS), *Bacillus thuringiensis* (SILoSil® BT) and *Trichoderma harzianum* (TRICHOSIL) microorganisms produce chitinolytic enzymes that are especially important at the beginning of the biodegradation. The chitinolytic enzymes help to degrade chitin containing solids which can constitute a barrier to further digestion. These organisms also produce proteases, lipases and other enzymes that facilitate the breakdown of proteins, lipids and carbohydrates.

As used herein, the term "HYTb refers to the aqueous fraction obtained from the biodegradation process. HYTb contains typically contains amino acids (about 3 wt % to 12 wt %, usually about 12 wt %), chitosan (about 1.2 wt %), glucosamine (about 1 wt %) and trace elements (about 6 wt %) including calcium, magnesium, zinc, copper, iron and manganese. The amount of chitosan can range between about 0.5 wt % and 1.5 wt %, more preferably between about 1.0 wt % and 1.5 wt %. The amount of glucosamine can range between about 0.5 wt % and 1.5 wt %, more preferably between about 1.0 wt % and 1.5 wt %. The total of chitosan and glucosamine is about 2.0 to 2.5 wt %. HYTb also contains enzymes such as lactic enzymes, proteases, lipases, chitinases, lactic acid, polypeptides and other carbohydrates. The specific gravity of HYTb is typically about 1.050-1.054. The average amino acid content in HYTb for certain amino acids is set forth in Table 1.

TABLE 1

Amino acid profile dry powder hydrolysates (mg per g dry weight)

| Amino acid | Dry powder hydrolysates |
|---|---|
| Aspartic acid | 38 |
| Glutamic acid | 39 |
| Serine | 16 |
| Histidine* | 9 |
| Glycine | 28 |
| Threonine* | 14 |
| Alanine | 36.1 |
| Proline | 25.8 |
| Tyrosine* | 70 |
| Arginine | 22.2 |
| Valine* | 20 |
| Methionine* | 16.4 |
| Isoleucine* | 18.3 |
| Tryptophan* | 3.1 |

TABLE 1-continued

Amino acid profile dry powder hydrolysates (mg per g dry weight)

| Amino acid | Dry powder hydrolysates |
|---|---|
| Leucine* | 23 |
| Phenylalanine* | 39 |
| Lysine* | 13 |
| Total | 431 |
| *Essential amino acids | 226 |

HYTb is typically produced by the centrifugation of the fermentation product formed by the biodegradation product. As the biodegradation process proceeds, nutrients for the microorganisms used for the biodegradation process, e.g. HQE, are depleted and the pH drops due to the acid produced during the fermentation. This causes the microorganisms in the fermentation product to die or become dormant. Depending on the g force and time of the centrifugation of the fermentation product, such microorganisms can be found in HYTb. Accordingly, HYTb can include any one or more of the above identified components, e.g. chitosan and glucosamine, in combination with all or part of the microbial component of the fermentation process that is present when it is stopped. Alternatively, the centrifugation may proceed to a point where substantially all of the microbial component is depleted from HYTb. In such cases the microbial component can be centrifuged into the HYTc fraction. Alternatively, HYTc can be separated from HYTb by low g centrifugation. The HYTb can then be centrifuged to form a pellet of microorganisms and a microorganism free-HYTb aqueous solution.

As used herein, the term "HYTc" refers to the solid fraction obtained from the biodegradation process. The primary component of HYTc is chitin. It typically has an average molecular weight of about 2300 daltons and constitutes about 64 wt % of the composition. About 6% of HYTc contains minerals including calcium, magnesium, zinc, copper, iron and manganese, about 24 wt % protein and 6% water. It has a specific gravity of about 272 Kg/m$^3$. The chitin in HYTc typically has microorganisms from the fermentation product associated with it. Chitinolytic microorganisms have a propensity to associate with solid chitin. This is based on the affinity of chitinolytic microorganisms for the chitin substrate. Accordingly, HYTc can also contain chitinolytic microorganisms unless steps are taken to remove them. In the case of HQE, such chitinolytic microorganisms include one or more of the chitinase and/or exochitinase producing microorganisms discussed herein. Such microorganism organisms include but are not limited to *Bacillus subtilis* (SILoSil® BS) *Bacillus thuringiensis* strains HD-1 and HD-73 (SILoSil® BT), and *Trichoderma harzianum* (TRICHOSIL). The chitinolytic microorganisms can be removed from the solid chitin by sterilization, pasteurization or washing the chitin with antimicrobial compounds sucg as soaps or chlorine. HYTc may also contain additional microorganisms present at the end of the biodegradation process because of the presence of residual fermentation product or the centrifugation of HYTb.

HQE Consortium

The following are the microorganisms in HQE which are believed to be involved in the biodegradation process and their known properties. In some cases the strain is identified as "Bioderpac, 2008". Where the species is not known, the species and strain are identified as "Bioderpac, 2008"

HQE was deposited with the ATCC on Apr. 27, 2010 and given Patent Deposit Designation PTA-10861.

*Bacillus subtilis* ((SILoSil® BS) is a Gram positive bacterium which is mesophilic and grows at an optimum temperature between 25 and 35° C. It is aerobic and can grow in anaerobic conditions and utilizes a wide variety of carbon sources. It contains two nitrate reductases, one of which is utilized for nitrogen assimilation. It is capable of secreting amylase, proteases, pullulanases, chitinases, xilanases and lipases.

*Bacillus thuringiensis* (Strains HD-1 and HD-73 (SILoSil® BT)) are Gram Positive anaerobic facultative bacteria, in the form of a peritrichous flagella. Strains HD-1 and HD-73 synthetizes crystals with diverse geometric forms of proteic and insecticide activity during the spore period. Strains HD-1 and HD-73 secret exochitanases when in a chitin containing medium and can be utilized for the degradation of the crustacean residues during the production of chitooligosaccharides.

*Bacillus cereus* (Bioderpac, 2008) is an aerobic facultative bacterium, gram positive, and spore forming. It is mesophilic and grows at an optimum temperature between 20 and 40° C. It produces the antibiotics zwittermicin A and kanosamin.

*Bacillus licheniformis* (Bioderpac, 2008) is a Gram-positive, motile, spore forming and facultative anaerobic bacterium. It produces bacitracin, alpha amylases, lactamases, proteases and alkaline phosphatases. This is a non-pathogen microorganism that is associated with plants or plant materials.

*Bacillus megaterium* (Bioderpac, 2008) is a Gram-positive aerobic bacterium. It is considered a saprophyte. It produces glucose dehydrogenase, penicillin amydase, beta-amidase and neutral proteases.

*Lactobacillus acidophilus* (Bioderpac, 2008) is a member of one of the eight species of lactic acid bacteria. It is Gram positive, non-sporulating and produces lactic acid during fermentation that utilizes lactose as a principal source of carbon to produce energy. It grows with or without the presence of oxygen in an acidic medium (pH 4-5). It produces the bactereocins named lactacin B, organic acids, diacetyls and hydrogen peroxide.

*Lactobacillus casei* (Bioderpac, 2008) is a mesophilic, facultative anaerobic which is Gram positive and non-spore forming. It has the ability to adapt to cold temperatures. The optimum pH for its growth is 5.5. It ferments galactose, glucose, fructose, manose, manitol, and acetylglucosamine. This species can be grown over a wide range of pH and temperature. It produces amylase enzymes. It inhibits the growth of pathogenic bacteria such as *H. pylori* by reducing pH through the production of (1) organic acids such as acetic, proprionic or lactic acid or (2) hydrogen peroxide. This microorganism secrets bacterocines.

*Pseudomonas fluorescens* (Bioderpac, 2008) is a bacteria with multiple flagellum, forced aerobic and its optimal temperature for growth is between 25 and 35° C. It produces thermostable lipases and proteases. It is antagonist towards a large number of soil fungus strains. It produces secondary metabolites such as antibiotics, iron chelates, and cyanides. It produces endochitanase and cellulase in mediums with different glucose concentrations.

*Trichoderma harzianum* (TRICHOSIL) is a saprophyte fungus. It exhibits antibiotic action and biological competition and for this reason has biological control properties. It produces enzymes that degrade cell walls or a combination of such activities. It produces glucanases, chitinases, lipases, and extracellular proteases when it interacts with some pathogenic fungi, such as *Fusarium*.

*Rhizobium japonicum* (Bioderpac, 2008) is a nitrogen fixating bacteria. It synthesizes a hydrogenase system that participates in the recycling of hydrogen to avoid its loss during nitrogen fixation.

*Azotobacter vinelandii* (Bioderpac, 2008) is an aerobic bacterium. It produces nitrogenases and is capable of nitrogen fixation.

*Clostridium pasteurianum* (Bioderpac, 2008) is a Gram positive bacteria, anaerobic obligated. It produces ferroxine (an electron transporting protein) that acts as a direct electron donor in the reduction of proteic iron.

*Proteus vulgaris* (Bioderpac, 2008) Is a gram positive bacteria, anaerobic, facultative that grows at temperatures close to 23° C. It proteolytically degrades proteins to free amino acids by the enzymes it produces.

*Streptomyces* sp. (Bioderpac, 2008) is a Gram-positive soil bacterium. It produces multiple enzymes that metabolize diverse nutrients. It can survive significant changes in temperature, humidity and nutrient sources. The extracellular enzymes produced by these bacteria utilize chitin and chitosan as substrates at a pH of 4.5 to 6.5 and at 60° C. These are conditions generated at the beginning and at the end stages of lactic fermentation in the biodegradation process.

*Nitrobacter* sp. (Bioderpac, 2008) is Gram negative bacteria, aerobic, which converts nitrites into nitrates. It grows at a pH between 6 and 9 and at temperatures between 10 to 34° C. The bacteria degrade organic polymers such as chitin into compounds that are utilized by other organisms, such as *Pseudomonas fluorescens*( ) and *Rhizobium japonicum* (Bioderpac2008).

*Micrococcus* sp. (Bioderpac, 2008) is a spheric Gram positive bacterium. This microorganism in association with *Streptomyces* sp( ) is capable of degrading colloidal chitin derivatives.

Groups and Enzymatic Activity of Microorganisms in HQE

The biodegradation of the components of marine animals or by-products requires hydrolytic enzymes such as proteases, lipases, and chitinases. The disclosed microbial compositions contain one or more of such enzymes.

The primary group of microorganisms in HQE are *Lactobacillus acidophilus* (Biodepac 2008), *Bacillus subtilis* (SILoSil® BS), *Pseudomonas fluorescens* (Biodepac 2008), *Bacillus licheniformis* (Biodepac 2008) and *Trichoderma harzianum* (TRICHOSIL). These microorganisms are capable of biodegrading arthropod or arthropod by-products. One or more of the members of this primary group also have a synergistic action when combined with other microorganisms from HQE.

The first group of microorganisms includes microorganisms which cause the reduction of pH and which stabilize fermentation due to the production of organic acids and hydrogen peroxide. This group includes *Lactobacillus acidophilus* (Biodepac 2008) and *Lactobacillus casei* (Biodepac 2008). Their activity is important at the start of fermentation and during the final stages of fermentation to produce the optimum pH for the hydrolytic enzymes. Their activity also creates a culture environment which prevents the growth of unwanted microorganisms and favors the demineralization of the chitin residues. *Lactobacillus acidophilus* (Biodepac 2008) is a member of the primary group.

The second group of microorganisms includes microorganisms which produce extracellular enzymes. This second group includes *Bacillus subtilis* (SILoSil® BS), *Bacillus cereus* (Biodepac 2008), *Trichoderma harzianum* (Biodepac 2008), *Rhizobium japonicum* (Biodepac 2008) and *Azotobacter vinelandii* (Biodepac 2008). The chitin chains in arthropod or arthropod by-products are associated with protein molecules. The separation of such polymers requires the hydrolytic action obtained from the chitinolytic and proteolytic enzymes produced by these microorganisms. Both types of enzymes break the chains on the internal portion of the polymer to produce oligomers of diverse sizes. The action from these enzymes occurs in a successive manner within the intermediate and final phases of the fermentation process when the appropriate pH conditions are achieved. The microorganisms on this group and the environmental conditions they produce facilitate the liberation of pigments and the lipid fraction adhered to these residues. *Bacillus subtilis* (SILo-Sil® BS) and *Trichoderma harzianum* (Biodepac 2008) are members of the primary group.

The third group of microorganisms includes the microorganisms *Bacillus licheniformis* (Biodepac 2008), *Pseudomonas flourescens* (Biodepac 2008), *Sptreptomyces*, (Biodepac 2008) and *Clostridium* (Biodepac 2008). These microorganisms hydrolyze oligomers (chito-oligosaccharides and peptides) to produce chitobioses, glucosamine, and free amino acids. *Bacillus licheniformis* (Biodepac 2008) and *Pseudomonas flourescens* (Biodepac 2008) are members of the primary group.

In preferred embodiments, one or two of the first, second and third groups of microorganisms can be combined. Alternatively, all of the first, second and third groups can be combined.

A fourth group of microorganisms includes *Bacillus thuringiensis* (strains HD-1 and/or HD-73), *Streptomyces* (Bioderpac, 2008), *Micrococcus* (Bioderpac, 2008), *Nitrobacter* (Bioderpac, 2008) and *Proteus vulgaris* (Bioderpac, 2008). The fourth group of microorganisms can be combined with (1) the primary group of microorganisms (2) any of the first, second and third groups of microorganisms (3) the combination of one or two of the first, second and third groups of microorganisms or (4) the combination of all of the first second and third groups. The addition of this fourth group results in a synergistic effect which enhances the biodegradation process.

Each of these groups, including the primary group, are separately useful and can be combined with prior art microbial compositions to enhance their performance. In this regard, the fourth group is particularly preferred.

Table 2 sets forth some of the aforementioned combinations. Column 1 is a list of the known microorganisms in HQE that are believed to be active in the biodegradation process. Column 2 lists the microorganisms from column 1 without the microorganisms in the fourth group of microorganisms. Column 3 shows the combination of the primary microorganisms while columns 4, 5 and 6 identify the combination of microorganisms from the first, second and third groups. Column 4 is the combination of groups 1 and 2; column 5 of groups 1 and 3 and column 6 groups 2 and 3. Other useful combinations are set forth in columns 7-10.

TABLE 2

| Microorganism | Culture Composition | | | | | | | | | |
|---|---|---|---|---|---|---|---|---|---|---|
| | 1 | 2 | 3 | 4 | 5 | 6 | 7 | 8 | 9 | 10 |
| Bacillus subtilis | X | X | X | X | | X | X | X | | X |
| Bacillus cereus | X | X | | X | | X | | X | | X |
| Bacillus megaterium | X | X | | | | | | | | |
| Azotobacter vinelandii | X | X | | X | | X | | X | | X |
| Lactobacillus acidophilus | X | X | X | X | X | | X | X | X | |
| Lactobacillus casei | X | X | | X | X | | | X | X | |
| Trichoderma harzianum | X | X | X | X | | X | X | X | | X |
| Rhizobium japonicum | X | X | | X | | X | | X | | X |
| Clostridium pasteurianum | X | X | | | X | X | | | X | X |
| Bacillus licheniformis | X | X | X | | X | X | X | | X | X |
| Pseudomonas fluorescens | X | X | X | | X | X | | | | |
| Bacillus thuringiensis | X | | | | | X | X | X | X | X |
| Streptomyces | X | | | | X | X | X | X | X | X |
| Nitrobacter | X | | | | | | | X | X | X | X |
| Micrococcus | X | | | | | | | X | X | X | X |
| Proteus vulgaris | X | | | | | | | X | X | X | X |

The activity of the enzymatic extracts produced by the microorganisms within HQE is complex, but has permitted the degradation of the chitinous residues of arthropods such as crustaceans. The microorganisms in HQE are activated in a successive manner according to the environment generated by the organisms used.

Methods for Identification and Isolation of Microbes in HQE

It is important to obtain pure isolates before attempting to characterize or identify a species. A few bacteria are morphologically unique and can be identified without isolation, but nearly all require isolation. The following describes the isolation of pure cultures from a mixture of species contained within HQE for *Bacillus subtilis* (SILoSil® BS), *Bacillus cereus* (Bioderpac, 2008), *Bacillus licheniformis* (Bioderpac, 2008), *Bacillus megaterium* (Bioderpac, 2008), *Lactobacillus acidophilus* (Bioderpac, 2008), *Lactobacillus casei* (Bioderpac, 2008), *Pseudomonas fluorescens* (Bioderpac, 2008), *Trichoderma harzianum* (strains HD-1 and HD-73), *Rhizobium japonicum* (Bioderpac, 2008), *Azotobacter vinelandii* (Bioderpac, 2008), *Clostridium pasteurianum* (Bioderpac, 2008), *Proteus vulgaris* (Bioderpac, 2008), *Bacillus thuringiensis* (SILoSil® BT), *Streptomyces* sp. (Bioderpac, 2008), *Nitrobacter* sp. (Bioderpac, 2008) and *Micrococcus* sp. (Bioderpac, 2008).

The first steps include:
(1) Dilution streaking and differential Incubations
(2) Identification and separation of colony types
(3) Narrowing down the collection, and
(4) Determining the initial characteristics of specific colonies and the preservation of Isolates.

Dilution Streaking and Differential Incubations

Once a specimen is removed from the HQE sample it should be cultured immediately. Any liquid sample must be thoroughly vortexed prior to preparation of the plates because non-motile bacteria may settle to the bottom of a sample if they are associated with particulate matter. Unfortunately, bacteria do not segregate homogeneously and replicate samples from the same mixture may contain different quantities of bacteria. The object of thorough vortexing and subsequent dilution streaking is to spread out individual CFUs (Colony Forming Units) so as to obtain discrete colonies that may be sub-cultured.

All of the mentioned microorganism can be separately subjected to the following procedures for identification and isolation with the exception of *Nitrobacter* sp. which will be explained separately.

A loop full of thoroughly vortexed sample from HQE is obtained aseptically and applied to one edge of the agar surface. With back and forth movements about one-fourth of the surface should be streaked while drawing the loop toward the middle of the plate. Streaking should not break the surface of the agar, and there should be (20 or more) streak lines produced. To dilute or spread out the sample the loop must be flamed to destroy all viable material, touched to a clean part of the agar to cool it, then streaks made perpendicular to the original inoculum, overlapping that part of the plate once or twice. The second section should cover one-half of the remaining sterile surface. This spreads out a small part of the original inoculum possibly diluting it sufficiently to result in the appearance of individual colonies after incubation. A third section is then streaked perpendicular to the second section, flaming and cooling the loop and overlapping the previous section as before, to further dilute the inoculum.

In the preparation of isolates from each batch of product, the next phase is to prepare replicate streak plates and incubate them under different conditions in an inverted position, to maximize opportunities to differentiate colony types for *Bacillus subtilis* (SILoSil® BS), *Bacillus cereus* (Bioderpac, 2008), *Bacillus licheniformis* (Bioderpac, 2008), *Bacillus megaterium* (Bioderpac, 2008), *Lactobacillus acidophilus* (Bioderpac, 2008), *Lactobacillus casei* (Bioderpac, 2008), *Pseudomonas fluorescens* (Bioderpac, 2008), *Trichoderma harzianum* (TRICHOSIL), *Rhizobium japonicum* (Bioderpac, 2008), *Azotobacter vinelandii* (Bioderpac, 2008), *Clostridium pasteurianum* (Bioderpac, 2008), *Proteus vulgaris* (Bioderpac, 2008), *Bacillus thuringiensis* (strains HD-1 and HD-73, SILoSil® BT), *Streptomyces* sp. (Bioderpac, 2008), and *Micrococcus* sp. (Bioderpac, 2008). The temperature of incubation is varied (typically 25, 30, and 37° C.) and incubated under both aerobic and anaerobic conditions. This approach increases the chances of separating individual species, since different species/bacterium have different optimum temperature ranges for growth and different requirements for oxygen. The aerobic organisms should be checked after one day of incubation, since some of our featured bacteria being tested grow very fast and crowd out the others.

Approaches to Identifying and Separating Colony Types

A dissecting microscope with a trans-illuminator can be used to distinguish individual colonies. Plates should remain inverted during examination. Colonies are distinguishable by size, shape, opacity, and texture regarding afore the mentioned microorganisms. Upon examination, it is best to indicate the colonies to be sampled by putting a small mark next to them on the bottom of the plate. It will be necessary to turn over the plate lid to collect colony material. Caution should be taken to carefully insert the sterile loop only for the time it takes to obtain an inoculum.

For color, surface characteristics and profile (raised, flat, etc.), it is necessary to examine the colonies with incident light, through the transparent lid. Lids should be left on otherwise the plates will become contaminated. Before turning the plate remove and invert the lid to remove the moisture. The old lid should be replaced with a new one for viewing.

In the event two colonies overlap and still can be distinguished, then at least two colonies are present. Colonies usually have a fairly simple, uniform texture. If an area resembles a mosaic, there are probably at least two species. Each unique type of colony should be sampled by taking a needle inoculum and performing a three way dilution streak on a fresh plate. Care should be taken to sample only the colony of interest. Incubate each new streak plate under aerobic conditions at the temperature which the original plate was incubated.

Species will exhibit temperature optima, indicated by faster growth and/or larger colonies at temperatures closest to ideal. Any colony that is sampled from an anaerobically incubated plate will likely be a facultative anaerobe.

Narrow Down the Collection

Duplicates of the same species and strain are likely to be isolated from different streak plates. Many different species and different strains of the same species produce very similar colony types. To narrow the number of isolates to unique species/strains, culture suspected duplicate isolates on the same plate. On two thirds of the surface conduct two "mini-dilutions" to obtain individual colonies for each culture, and on the remaining one-third mix them. After incubation, if the two isolates grow on the same plate and/or mixed inoculum produce two distinguishable colony types, two unique isolates have been identified.

Initial Characterization of Colonies and Preservation of Isolates

Most of the characteristic of the organisms under consideration should be determined using incident, not transmitted, light.

Once an isolate is obtained and purity established by both colony examination and microscopic examination, an agar slant tube should be inoculated and incubated at an appropriate temperature with the cap loose to allow gas exchange. After growth appears, the culture should be described, the cap tightened, and the tube kept at room temperature as a source of pure culture for assays.

In addition to gross descriptive characterization, a young (<18 h) culture should be gram stained and the results recorded including cell shape and size, sheaths or capsules if evident, and any evidence of spores or similar structures. Relationship to oxygen is the next step with which to narrow possible categories. After that, it is this particular combination of Gram stain results, cell type, and relationship to oxygen that determines the next series of steps toward characterizing the isolate.

The Deletion and Counting of *Nitrobacter* sp. Population in the Product

There have been several studies on the metabolism, survival, and growth of nitrite oxidizers in pure cultures and on their nitrifying activity in various environments, but fewer studies have dealt with natural *Nitrobacter* population. Although the biological conversion of nitrite to nitrate is a well known process, studies and procedures of the *Nitrobacter* population are currently hampered by inadequate methods of detection and counting.

This failure is due in part to the unfavorable physiological characteristics of these bacteria, namely slow growth, small biomass, and susceptibility of cultures to contamination. There is a way to count *Nitrobacter* population in the soil but it is time consuming and selective.

Detailed Description of the Growth Process

*Bacillus cereus* (Bioderpac, 2008), *Bacillus megaterium* (Bioderpac, 2008),

*Bacillus subtilis* (SILoSil® BS) and *Bacillus licheniformis* (Bioderpac, 2008)

Media ingredient: purified water and plate medium nutrient agar.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is nutrient agar, (4) incubate plates at 37° C. for 24-48 hours, (5) colony forming units should be 1,000,000 per 1 ml of product.

*Pseudomonas fluorescens* and *Proteus vulgaris*

Media ingredient: purified water and plate medium nutrient agar.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is nutrient agar, (4) incubate plates at 37° C. for 24-48 hours, (5) colony forming units should be 1,000,000 per 1 ml of product.

*Lactobacillus acidophilus* and *Lactobacillus casei*

The Agar M.R.S. was developed by Man, Rogosa and Sharpe to provide means that could demonstrate a good growth of *lactobacillus* and other lactic acid bacteria. The culture medium allows an abundant development of all the species of *lactobacillus*. Peptona and glucose constitute the nitrogen source, carbon and of other necessary elements for the bacterial growth. The sorbitan monoleate, magnesium, manganese and acetate, contribute cofactors and can inhibit the development of some microorganisms. The ammonium citrate acts like an inhibiting agent of the growth of negative Gram bacteria. See Table 3.

TABLE 3

| Formula (in grams per liter) | | Instructions |
|---|---|---|
| Proteose peptone N° 3 | 10.0 | Suspend 64 g of the medium in a liter of distilled water. Let it rest 5 minutes and mix warming up to boiling point during 1 or 2 minutes. Sterilize in sterilizer during 15 minutes to 121° C. |
| Meat extract | 8.0 | |
| Yeast extract | 4.0 | |
| Glucose | 20.0 | |
| Sorbitan Monoleate | 1 ml | |
| Dipotassium Phosphate | 2.0 | |
| Sodium Acetate | 5.0 | |
| Ammonium Citrate | 2.0 | |
| Magnesium Sulfate | 0.2 | |
| Manganese Sulfate | 0.05 | |
| Agar | 13.0 | |

Final pH: 6.4 ± 0.2

Media ingredient: purified water and plate medium nutrient agar M.R.S substrate.

Procedure: (1) place 0.1 ml liquid sample of HQE in 9.9 ml of purified water, (2) commence a serial dilution range up to 1-10, (3) incubate into aerobic chamber with 5-10 $CO_2$ a replicate plate series with 1 ml of the dilution range, the plate medium is agar M.R.S., (4) incubate plates at 33-37° C. for 72 hours or 30° C. for 5 days, (5) colony forming units should be 1,000,000 per 1 ml of product.

Results. Colony forming units should be 1,000,000 per 1 ml of product.

Characteristics of the colonies: generally small, white-grayish, smooth or rough.

Characteristics of the medium: Prepared medium is yellow.

*Lactobacillus* identification:

TABLE 4

| | Growth at | | Acid | | | | | $NH_3$ | Growth in 4% |
|---|---|---|---|---|---|---|---|---|---|
| | 15° C. | 45° C. | la | su | sal | mn | so | xi | Arginine | NaCl broth |
| L. acidophilus | − | + | + | + | + | − | − | − | − | − |
| L. casei | + | V | +/− | +/− | + | + | + | − | − | + |

*Azotobacter vinelandii* (Bioderpac, 2008)

Media ingredient: purified water and plate medium nutrient agar substrate (Burk's, Asbhy, Jensen's).

Procedure: (1) place 0.1 ml liquid sample of HQE in 9.9 ml of purified water, (2) incubate this solution at 25° C. for 48 hours, (3) commence a serial dilution range up to 1-10, (4) incubate a replicate plate, with nutrient agar substrate, series with 1 ml of the dilution range, the plate medium is nutrient agar (5) incubate plates at 25° C. for 48-72 hours, (6) colony forming units should be 1,0000,000 per 1 ml of product.

*Clostridium pasteurianum* (Bioderpac, 2008)

Media ingredient: phosphate buffered water and plate medium standard methods agar substrate (TYG).

Procedure: (1) place 0.1 ml liquid sample of HQE in 9.9 ml of phosphate buffered water, (2) make appropriate serial dilutions (3) plate appropriate aliquot for desired dilution into Petri dishes, (4) add tempered standard methods agar and mix of dish, (5) place inverted dried plates into anaerobic chamber, (6) incubate plates at 35-37° C. for 48-72 hours, (7) after incubation period, removed plates from anaerobic chamber and count plates, record dilutions used and the total number of colonies counted for each dilution, (8) colony forming units should be 1,000,000 per 1 ml of product.

The identification of this species of *Clostridium* uses a typical microscopic morphology of a colony which allows a fast and presumptive identification of some species of *Clostridium* frequently isolated. In addition, along with the use of simple biochemical tests such as the study of the production of lecitinase and lipase in agar egg yolk, the hydrolysis of the gelatin and urea and the production of indol through the fast method (p-dimetil-amino-cinnamaldehide), constitute an easy and inexpensive method for the identification, even definitive, for some of them.

*Micrococcus* sp. (Bioderpac, 2008)

Media ingredient: purified water and plate medium nutrient agar.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is nutrient agar, (4) incubate plates at 37° C. for 24 hours, (5) colony forming units should be 1,000,000 per 1 ml of product.

If positive Gram coccos are found, perform antibiotic sensitivity tests. *Micrococcus* is sensitive to Bacitracin and resistant to furazolidone.

*Rhizobium japonicum* (Bioderpac, 2008)

Media ingredient: purified water and plate medium ALM (agar yeast extract mannitol).

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is ALM (agar yeast extract mannitol), (4) incubate plates at 28° C. for 96 hours, (5) colony forming units should be 1,000,000 per 1 ml of product.

To confirm *Rhizobium japonicum* (Bioderpac, 2008), the isolated colony is used to infect a leguminosae aseptically to cause the formation of nodules.

*Trichoderma harzianum* (TRICHOSIL)

Media ingredient: purified water and malt extract agar medium (2% wt/vol) substrate supplemented with chloramphenicol, streptomycin sulfate, and nystatin.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is malt extract agar (4)

incubate plates at 25° C. for 4 days, (5) colony forming units should be 1,000,000 per 1 ml of product.

*Bacillus thuringiensis* (Strains HD-1 and HD-73 (SILo-Sil® BT))

Media ingredient: purified water and plate Superbroth medium agar substrate supplemented with 2 g/litro de D-glucosa and 50 μg/ml erythromycin.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is Superbroth agar (4) incubate plates at 28° C. for 10-14 days, (5) colony forming units should be 1,000,000 per 1 ml of product.

*Streptomyces* sp. (Bioderpac, 2008)

Media ingredient: purified water and plate actinomycete isolation agar medium.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is actinomycete isolation agar (4) incubate plates at 28° C. for 2-3 days, (5) colony forming units should be 1,000,000 per 1 ml of product.

*Nitrobacter* sp. (Bioderpac, 2008)

Media ingredient: purified water and plate medium nutrient agar substrate.

Procedure: (1) place 0.1 ml liquid sample of HQE in 9.9 ml of purified water, (2) commence a serial dilution range up to 1-10, (3) incubate a replicate plate series with 1 ml of the dilution range, the plate medium is plate nutrient agar substrate, (4) incubate plates at 30° C. for 10-14 days.

Biodegradation Process

In a preferred embodiment, the marine arthropod is a crustacean and the preferred crustacean is shrimp. Shrimp by-product comprises shrimp cephalothorax and/or exoskeleton.

In the biodegradation process, it is preferred that the fermentation be facultative aerobic fermentation. It is also preferred that the fermentation is carried out at a temperature of about 30° C. to 40° C. The pH is preferably less than about 6, more preferably less than about 5.5. However, the pH should be maintained above about 4.3. The fermentation is carried out for about 24-96 hours. In some embodiments, the fermentation is carried out for about 24-48 hours and more preferably 24-36 hours. These fermentation times are far shorter than the typical prior art fermentation times of 10 to 15 days to achieve substantially the same amount of digestion, albeit without detectable formation of chitosan and glucosamine.

The separation of the mixture is preferably by centrifugation. (e.g. about 920 g). Gravity separation can also be used but is not preferred because of the time required to achieve separation.

The mixture separates in to three fractions: solid, aqueous and lipid. The solid fraction comprises chitin and is designated HYTc. The aqueous fraction comprises protein hydroysate, amino acids, chitosan and glucosamine and is designated HYTb. The lipid fraction comprises sterols, vitamin A and E and carotenoid pigments such as astaxanthine.

Any of the microbial compositions identified herein can be used in the biodegradation process, In some embodiments it is preferred that HQE be used in the biodegradation process. In other embodiments, it is preferred that HYTb be added to HQE or the fermentation broth. As described above, HYTb contains amino acids, chitosan, glucosamine and trace elements including calcium, magnesium, zinc, copper, iron and manganese. HYTb also contains enzymes such as lactic enzymes, proteases, lipases, chitinases, lactic acid, polypeptides and other carbohydrates. HYTb can also contain dormant microorganisms from a prior biodegradation process. Such microorganisms can become reactivated and, in combination with HQE, contribute to a more robust biodegradation process as compared to when HQE is used by itself as otherwise described herein More particularly, the process includes the following steps:
a. Activation of the microbial cells in a sugar base solution to enhance its growth and the biomass formation.
b. Milling of the shrimp by-products (cephalthorax and exosqueleton) to make a homogeneous paste.
c. Homogeneous mixing of the shrimp by-product paste with at least 10% of the activated inoculum.
d. Adjustment of the pH values to less than 6.0 in the mixture using a citric acid solution to inhibit the growth of micro organisms and to promote the development of microbial cells that constitute the inoculum.
e. Fermentation of the mixture in a non continuous agitated system at temperatures within a range of 30 to 40° C. at least for at least 96 hours maintaining pH at less than 5.0. The pH is monitored periodically. If the pH rises above 5.0, a citric acid buffer is added in an amount to maintain the pH below 5.0.
f. Centrifugation of the ferment to separate the three principal fractions: chitin, liquid hydrolysate and pigmented paste.
g. Rinsing of the crude chitin and recollection of the rinse water to recuperate fine solids or minerals.
h. Drying of the chitin and storage.
i. Drying and storage of the liquid hydrolysate.
j. The pigmented paste (lipid fraction) is stored in closed recipients for conservation.

The process and operational fundamentals are better understood with reference to FIG. 1 and the following detailed description.

Activation of Microbial Cells

A microbial composition as disclosed herein is used as inoculum. The inoculum of HQE has a concentration of microbes of about 2.5 to 3.0% (w/v). HQE is activated by dilution to 5% in sugar cane solution (3.75% final concentration of sugar cane), and incubated at 37° C. for 5 days. HYTb (10 ml per liter of culture) is preferably added to provide a source of minerals and naturally derived amino acids. The cellular growth of the microorganisms was estimated by optical density measured at 540 nm. The activation is complete at an optical density of about 1.7. The concentration of microbes after activation is about 1.9 to 3.0% (w/v).

Preparation of Samples

The shrimp by-products samples are obtained from shrimp processing plants. Slightly thawed and minced residue (1500 g by batch) is mixed with 99 grams of sugar cane (final concentration 6.6% wt %) and 85.5 ml of activated HQE 5% (v/w) (optical density of cell=1.7). Then the pH is adjusted to 5.5 using 2 M citric acid.

Fermentation Control

The mixture is incubated at 36° C. with a non continuous agitation for 96 h. During the fermentation process, the pH is monitored by using a potentiometer, and the total titratable acidity (TTA, %) was determined by titration with 0.1 N NaOH until a pH of 8.5 is obtained. The TTA is expressed as a percentage of lactic acid.

Conditions of Separation

The fermentation product is a viscous silage which has an intense orange color, due to the astaxanthine presence. The ensilage is centrifuged (5° C.) at 1250 rpm (930 g) for 15 min to obtain the chitin, the liquid hydrolysates, and the pigment paste. The upper phase (pigment paste) is separated manually. The liquid hydrolysates are separated by decantation, and the sediment that constitutes the raw chitin is washed with distilled water to separate fine solids. The resulting liquid is collected and dried. The raw chitin, liquid hydrolysates and fine solids are dried at 60° C. All the fractions are stored to protect them from light.

The above protocol was carried out using HQE in three fermentation batches in duplicate as set forth in the following examples.

Example 1

Fermentation control by measurement of pH and total titratable acidity (TTA, %)

Figure 2:
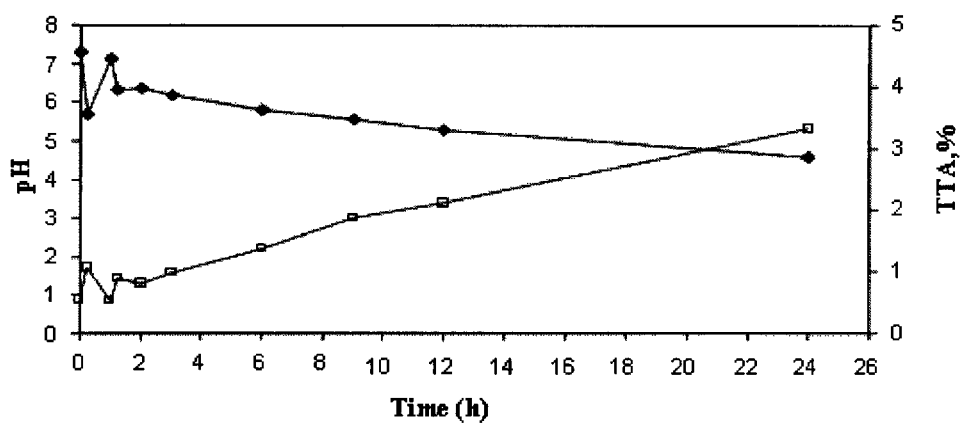
FIG. 2 depicts the pH and total titratable acidity during lactic fermentation of the shrimp by-products.

The average initial values of pH and TTA were 7.31±0.10 and 0.53±0.09, respectively. As shown in FIG. 2, the pH was initially reduced to 6.5 by the addition of 2 M citric acid. Then, due to proteolysis and the release of ammonium, the pH increased again to 7.11±0.08 during the first 2 h, and later, the pH diminished by 28% (up to 5.28±0.01) during the 12 hours of fermentation. At approximately 24 hours of fermentation, the final pH was 4.57±0.15. In parallel to the decrease in pH a similar behavior was observed in the mean values of the TTA. During the first 2 hours of the average values of TTA were 1%, and then these values increased gradually to an average value of 3.33±0.23 at 24 hours, as shown in FIG. 2.

Example 2

Products of the Fermentation and Chemical Composition

After the fermentation process, the silage was centrifuged to separate the three principal products (chitin, liquid hydrolysate, and pigment paste). The other product, the fine solids were retained with the raw chitin wash. Table 5 shows the proportion recovered in each fraction. In dry weight, the bigger fraction corresponded to the liquid hydrolysate (55%), then the fine solids (29%), raw chitin (10%) and pigment paste (5%). In the fermented batch, the average value of dry weight was 32% (481.1±5.6 g).

Table 6 shows the chemical characterization of each of the four main products that were obtained through fermentation. The chitinous product (chitin) shows a partial demineralization reflected as ash. It also reveals high protein content (42.34%) quantified in the liquid hydrolysates. This facilitated the recovery of a pigment paste, consisting mainly of total lipids (42.67%), and produced a fraction abundant in ash (16.72%) in the fine solids.

TABLE 5

Products separated from fermentation

| Dry matter (g) | Raw chitin (g) | Liquid hydrolysate (g) | Lipidic paste (g) | Fine solids (g) |
|---|---|---|---|---|
| 480.0 | 48.0 | 264.4 | 22.9 | 141.2 |
| 487.5 | 50.2 | 268.8 | 24.0 | 140.8 |
| 475.7 | 51.0 | 265.7 | 23.7 | 131.7 |
| 481.1 ± 5.6 | 49.5 ± 2.4 | 266.3 ± 4.6 | 23.3 ± 0.5 | 141.9 ± 5.5 |

TABLE 6

Chemical composition (dry weight) of the fermentation products

| Products | % Protein | % Ash | % Total lipid |
|---|---|---|---|
| Raw chitin | 18.12 ± 0.15 | 4.36 ± 0.26 | 2.02 ± 0.46 |
| Liquid hydrolysate | 42.34 ± 0.03 | 7.96 ± 0.16 | 4.28 ± 0.28 |

TABLE 6-continued

Chemical composition (dry weight) of the fermentation products

| Products | % Protein | % Ash | % Total lipid |
|---|---|---|---|
| Lipidic paste | 30.80 ± 0.25 | 5.11 ± 0.16 | 42.67 ± 0.63 |
| Fine solids | 31.62 ± 0.10 | 16.72 ± 0.37 | Nd |

Example 3

Amino Acid Profile in the Dry Powder Hydrolysates

The amino acid content of dried hydrolysate was determined as described by Lopez-Cervantes et al., "Analysis of free amino acids in fermented shrimp waste by high-performance liquid chromatography", Journal of Chromatography A, volume 1105, 1 (2006). Table 6 shows the total amino acid profile of the dry powder hydrolysates. The proportion of essential amino acids was of 52.5% to dry powder hydrolysates.

TABLE 7

Amino acid profile dry powder hydrolysates (mg per g dry weight)

| Amino acid | Dry powder hydrolysates |
|---|---|
| Aspartic acid | 38 |
| Glutamic acid | 39 |
| Serine | 16 |
| Histidina* | 9 |
| Glycine | 28 |
| Threonine* | 14 |
| Alanine | 30 |
| Proline | 8 |
| Tyrosine* | 70 |
| Arginine | 18 |
| Valine* | 20 |
| Methionine* | 4 |
| Isoleucine* | 15 |
| Leucine* | 23 |
| Phenylalanine* | 39 |
| Lysine* | 13 |
| Total | 394 |
| *Essential amino acids | 207 |

Example 4

Quantification of Glucosamine in Raw Chitin

In the chitin, the content of glucosamine was quantified as an index of purity. The contents of glucosamine in chitin were 516, 619 and 640 mg per g (dry weight), these values correspond to the results of three fermentation batches carried out in duplicate. Therefore, the average amount of glucosamine in this study was 591 mg per g dry weight of chitin. The method for quantification of glucosamine was reported by Lopez-Cervantes et al., "Quantitation of glucosamine from shrimp waste using HPLC" Journal of Chromatographic Science, volume 45, 1 (2007).

Example 5

Contents of Astaxanthin and Profile of Fatty Acids in Pigment Paste

Astaxanthin is the main pigment in the lipidic paste obtained from fermented shrimp waste. The content of astaxanthin ranged from 1.98 to 2.25 mg g$^{-1}$ of dry lipidic paste, and the average is 2.11 mg g$^{-1}$ of dry lipidic paste. Astaxanthin was determined by a version of the method of Lopez-Cervantes et al., "Quantification of astaxanthin in shrimp waste hydrolysate by HPLC" *Biomedical Chromatography*, volume 20, 981 (2006).

In the pigment paste, fourteen fatty acids were identified. The palmitic acid (C16:0), and the oleic acid (C18:1n9) were found in higher quantity.

What is claimed is:

1. A biodegradation process comprising:
   mixing a marine animal or marine animal by-product with a microbial composition comprising the microbes in ATCC Patent Deposit Designation PTA-10861 to form a mixture;
   fermenting said mixture; and
   separating said mixture into solid, aqueous and lipid fractions;
   wherein said microbes comprise *Bacillus subtilis, Bacillus thuringiensis, Bacillus cereus, Bacillus licheniformis, Bacillus megaterium, Lactobacillus acidophilus, Lactobacillus casei, Pseudomonas fluorescens, Trichoderma harzianum, Rhizobium japonicum, Azotobacter vinelandii, Clostridium pasteurianum, Proteus vulgaris, Streptomyces* sp., *Nitrobacter* sp. and *Micrococcus* sp.

2. The process of claim 1 wherein said marine animal is a marine arthropod.

3. The process of claim 2 wherein said marine arthropod is selected from the group consisting of shrimp, crab and krill.

4. The process of claim 1 wherein said marine animal is fish.

5. The process of claim 1 wherein said fermenting is by facultative aerobic fermentation.

6. The process of claim 1 wherein said separating is by centrifugation.

7. The process of claim 1 wherein said fermenting is at a temperature of about 30° C. to 40° C.

8. The process of claim 7 wherein said fermenting is carried out at a pH between about 4.3 and 5.0.

9. The process of claim 7 wherein said fermentation is carried out for about 24-96 hours.

10. The process of claim 1 wherein said aqueous fraction comprises amino acids, chitosan and glucosamine.

11. The process of claim 10 wherein said aqueous fraction further comprises trace elements.

12. The aqueous fraction made according to claim 1.

13. The process of claim 1 wherein said solid fraction comprises chitin.

14. The solid fraction made according to claim 13.

* * * * *